United States Patent [19]

Wogoman

[11] Patent Number: 4,990,075
[45] Date of Patent: Feb. 5, 1991

[54] REACTION VESSEL FOR PERFORMING SEQUENTIAL ANALYTICAL ASSAYS

[75] Inventor: Frank W. Wogoman, So. Bend, Ind.

[73] Assignee: Miles Inc., Elkhart, Ind.

[21] Appl. No.: 179,843

[22] Filed: Apr. 11, 1988

[51] Int. Cl.$^5$ .............................. G01N 33/52
[52] U.S. Cl. ...................... 422/58; 422/55; 422/58; 422/61; 422/72; 422/102; 436/518; 436/526; 436/528; 436/533; 436/45; 436/67; 436/165; 436/807; 435/299; 435/312
[58] Field of Search ............. 422/55, 56, 58, 61, 422/72, 102; 436/45, 43, 66, 67, 165, 169, 180, 805, 807, 809; 435/299, 312

[56] References Cited

U.S. PATENT DOCUMENTS

| 4,673,653 | 6/1987 | Guigan | 436/8 |
| 4,780,285 | 10/1988 | Kuypers | 422/102 |

FOREIGN PATENT DOCUMENTS

| 213653 | 8/1985 | European Pat. Off. |
| 197865 | 3/1986 | European Pat. Off. |
| 3706718 | 3/1987 | Fed. Rep. of Germany |
| 2589240 | 10/1985 | France |

Primary Examiner—Robert J. Warden
Assistant Examiner—David Redding
Attorney, Agent, or Firm—Daniel W. Collins; Andrew L. Klawitter

[57] ABSTRACT

Analytical reagent reaction vessel and method for performing sequential analytical assay procedures to determine an analyte in a liquid test sample. The reaction vessel is in the form of a closed container having a substantially horizontal axis of rotation and incorporated with one or more analytical reagents for performing a desired analytical assay procedure. The reaction vessel is designed to provide free gravitational movement of a liquid test sample disposed therein. The analytical reagents are incorporated into the reaction vessel such that they are contacted with a liquid test sample in a desired order or sequence. A liquid test sample disposed in the reaction vessel is capable of being manipulated therein by rotating the reaction vessel about the horizontal axis wherein the liquid test sample is transported by gravity. Accordingly, a liquid test sample can be sequentially contacted with the analytical reagents, and one or more of a detectable response can be measured, without the need for additional external manipulative steps or complicated instruments to complete the assay. The reaction vessel is particularly useful for performing immunoturbidimetric and immunometric assays.

54 Claims, 5 Drawing Sheets

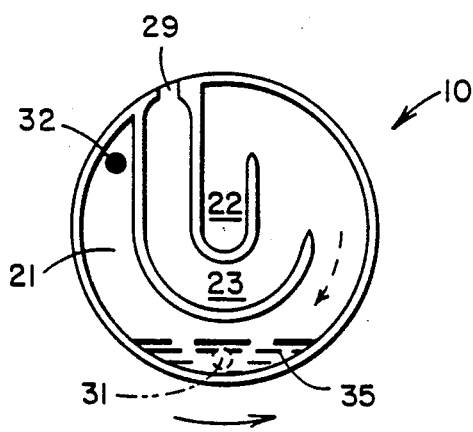
FIG. 4g
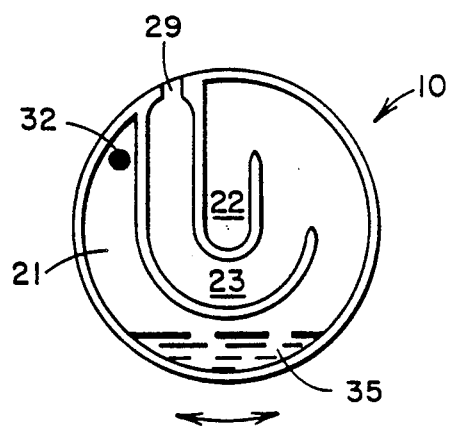
FIG. 4h
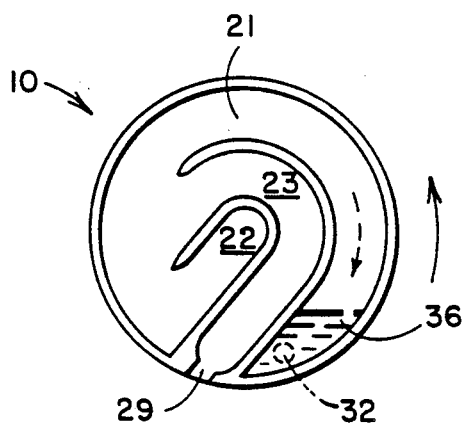
FIG. 4i
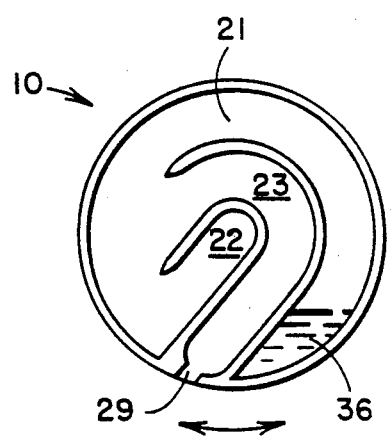
FIG. 4j
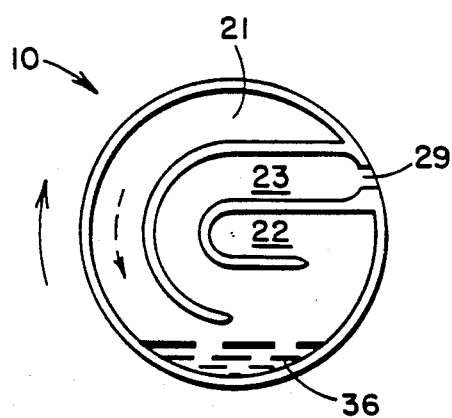
FIG. 4k
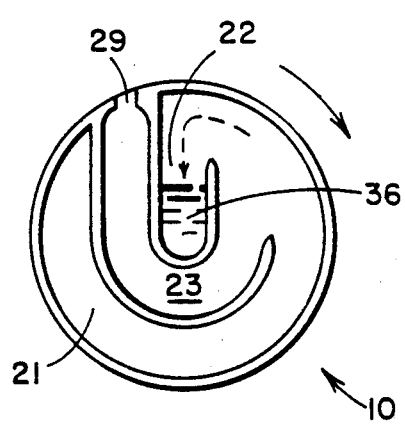
FIG. 4ℓ

REACTION VESSEL FOR PERFORMING SEQUENTIAL ANALYTICAL ASSAYS

BACKGROUND OF THE INVENTION

The present invention relates to analytical assay procedures for determining the amount of an analyte present in a liquid test sample. In particular, the present invention relates to the determination of an analyte in a liquid test sample involving analytical reactions between the analyte and one or more analytical reagents requiring sequential, manipulative steps to make such determination.

Various analytical procedures have been developed for the determination of analytes of industrial, environmental and particularly medical significance. In many instances, such analytical procedures involve a number of analytical reactions and manipulative steps which must be performed sequentially in order to carry out an assay protocol. Such sequential steps, including such manipulations as pipetting, centrifugation, periods of incubation, separation steps, and the like, are subject to errors that can lead to inaccurate results. Although various devices have been developed in an attempt to automate or otherwise simplify such manipulative steps, such devices are often cumbersome and require trained, experienced technicians for their operation. In some instances, such devices still require a number of manual manipulative steps during the course of carrying out an assay protocol.

For example, U.S. Pat. No. 4,673,653 describes a method for performing biological analysis of a liquid sample employing a compartmentalized plastic container which requires a number of centrifugation steps. The container comprises a storage chamber for the liquid sample, a calibration cell, a plurality of storage chambers for various reaction liquids, and a reaction vat. The various chambers, calibration cell and reaction vat are interconnected by capillary ducts for communicating liquids therebetween by centrifugal force. In carrying out the biological analysis, successive centrifugation steps are performed with the angular position of the container being selected for each centrifugation step as a function of the orientation of a particular capillary duct relative to the direction of the centrifugal force in order to facilitate manipulation of a liquid disposed in the device.

U.S. Pat. No. 4,690,801 describes a manually manipulated device comprising a disk having a thin flexible membrane applied to one side thereof which defines a conduit and a plurality of reagent reservoirs isolated from one another by frangible seals. An assay tube is situated at one end of the conduit and a sample injection reservoir is situated at the other end of the conduit. The disk fits into a base member, and a cover member having a roller bar fits over the base wherein the roller bar engages the surface of the disk. In operating the device, the cover is rotated relative to the disk wherein the roller bar applies pressure to the reservoirs to rupture the frangible seals and force the reagents from their respective reservoirs into the conduit for the purpose of carrying out the assay.

Accordingly, it is an object of the present invention to provide a device for performing sequential analytical assay procedures which does not involve centrifugation or other mechanically generated forces.

Another object of the present invention is to provide a device for performing sequential analytical assay procedures which requires a minimal number of manual manipulation steps.

Further, it is an object of the present invention to provide a device for performing sequential analytical assay procedures which does not involve complicated manufacturing or assembly processes.

Still another object of the present invention is to provide a device for performing sequential analytical assay procedures which is easy to manipulate and operate.

Still further, another object of the present invention is to provide a device for performing sequential analytical assay procedures which is easily adaptable to a physician's office or a small, clinical laboratory.

SUMMARY OF THE INVENTION

The present invention provides a self-contained analytical reagent reaction vessel or device and method for performing analytical assay procedures involving sequential analytical reactions between an analyte in a liquid test sample and one or more analytical reagents which interact with the analyte to produce a detectable response as a function of the analyte. The device is particularly useful for performing immunoassays which typically require a number of cumbersome manipulative steps, such as pipetting, mixing and incubation of the liquid test sample with the analytical reagents, and detection. The necessary sequential steps are accomplished within the device simply by non-centrifugal rotation of the device, resulting in gravitational flow of the test sample or reaction mixture to zones or areas in the device designed for performing the various functional steps of the assay.

According to the present invention, the device is incorporated with one or more of the necessary analytical reagents for carrying out a particular sequential analytical assay procedure wherein a liquid test sample introduced into the device can be sequentially contacted and reacted with the analytical reagents without the need for additional external manipulative steps to complete the assay. The device also permits the convenient measurement of the detectable response produced by analytical reactions between the analyte and the analytical reagents and, where one or more detectable responses are produced subsequent to or during the performance of the assay, the device can be easily manipulated to permit the convenient measurement thereof in the device during the course of the assay. Manipulation of a liquid test sample and analytical reagents in the device does not involve centrifugation or other mechanically generated forces, and can therefore be manipulated manually or with a simple, uncomplicated instrument.

In particular, the device comprises a closed container having a substantially horizontal axis of rotation, preferably a substantially central axis of rotation, and comprising an analytical reagent reaction channel, liquid test sample delivery means for providing unidirectional flow of a liquid test sample into the reaction channel, preferably in the form of a delivery chamber, and inlet means in open liquid flow communication with the delivery means for introducing a liquid test sample into the delivery means, preferably in the form of an inlet port. The analytical reagent reaction channel comprises one or more reaction zones incorporated with one or more analytical reagents, preferably as a dry form thereof, respectively. For example, where a particular analytical assay procedure requires two analytical reagents to carry out the assay, a first analytical reagent can be incorporated into a first reaction zone and a second analytical reagent can be incorporated into a second reaction zone, the second reaction zone being situated a predetermined distance away from and in open liquid flow communication with the first reaction zone. The analytical reagent reaction channel can further include an analytical reaction viewing zone situated at a predetermined location in the reaction channel, preferably in the form of a viewing chamber situated at one end of and in open liquid flow communication with the reaction channel, from which the detectable response produced by a liquid test sample or an analytical reaction mixture thereof can be detected and measured.

According to the present invention, a liquid test sample disposed in the reaction channel can be transported by gravity along the reaction channel between one or more reaction zones and the viewing zone by rotating the device about the horizontal axis of rotation of the device. Accordingly, once a liquid test sample has been introduced into the device, an analytical assay procedure can be carried out by simply rotating the device as described above without the need for additional pipetting, centrifugation, or otherwise complicated manipulative steps to transfer the liquid test sample from one analytical reagent to another or, for example, to a cuvette for detecting and measuring the detectable response.

An analytical assay procedure employing the device of the present invention is performed by introducing a liquid test sample into the delivery means through the inlet means wherein the liquid test sample flows from the delivery means into the reaction channel by gravity, preferably by rotating the device about the horizontal axis. The liquid test sample is brought into contact with the first analytical reagent in the first reaction zone, preferable by rotating the reaction zone about the horizontal axis whereby the liquid test sample is transported by gravity along the reaction channel into the first reaction zone, to form a first reaction mixture with the first analytical reagent incorporated therein. The first reaction mixture is then immediately or after an incubation or reaction period transported by gravity away from the first reaction zone along the reaction channel and brought into contact with the second analytical reagent in the second reaction zone by rotating the device about the horizontal axis to form a second reaction mixture with the second analytical reagent incorporated therein. Where, for example, the second reaction mixture produces the detectable response, the second reaction mixture can be transported by gravity away from the second reaction zone along the reaction channel and into the viewing zone by rotating the device about the horizontal axis. The detectable response can then be measured from the viewing zone and correlated to the amount of analyte present in the liquid test sample.

As will be described in greater detail hereinafter, the device of the present invention is not intended to be limited to analytical assay procedures involving two analytical reagents as described above, but can be employed to carry out substantially any sequential analytical assay procedure involving a single analytical reagent or one or more additional analytical reagents. In addition to providing for the sequential contact of one or more additional analytical reagents in the reaction channel, the open liquid flow communication provided between the reaction channel and the viewing zone permits the measurement of one or more of an additional detectable response in a desired ordered sequence by rotating the device about the horizontal axis whereby a liquid test sample or one or more additional analytical reaction mixtures thereof can be transported by gravity between the reaction channel and the viewing zone for multiple measurements during the course of a single assay.

BRIEF DESCRIPTION OF THE DRAWINGS

FIG. 4(a) to 4(l) are front views of the device shown in FIG. 2 illustrating the various steps for performing a sequential analytical assay procedure with the device of the present invention.

DESCRIPTION OF THE PREFERRED EMBODIMENTS

Figure 2:
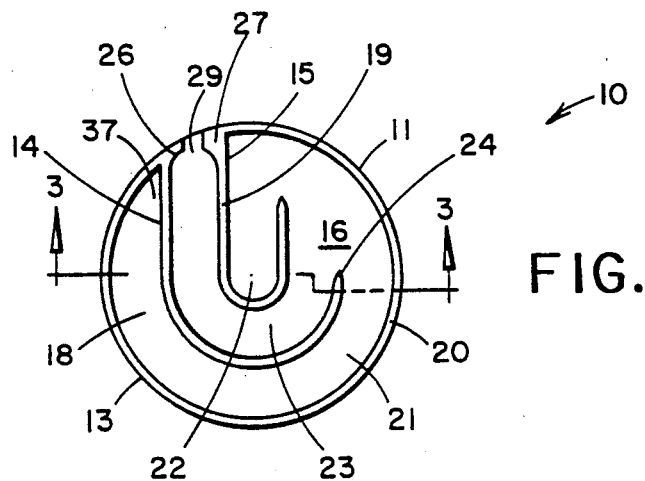
FIG. 2 is a front view of the device shown in FIG. 1 without its lid member.
Figure 1:
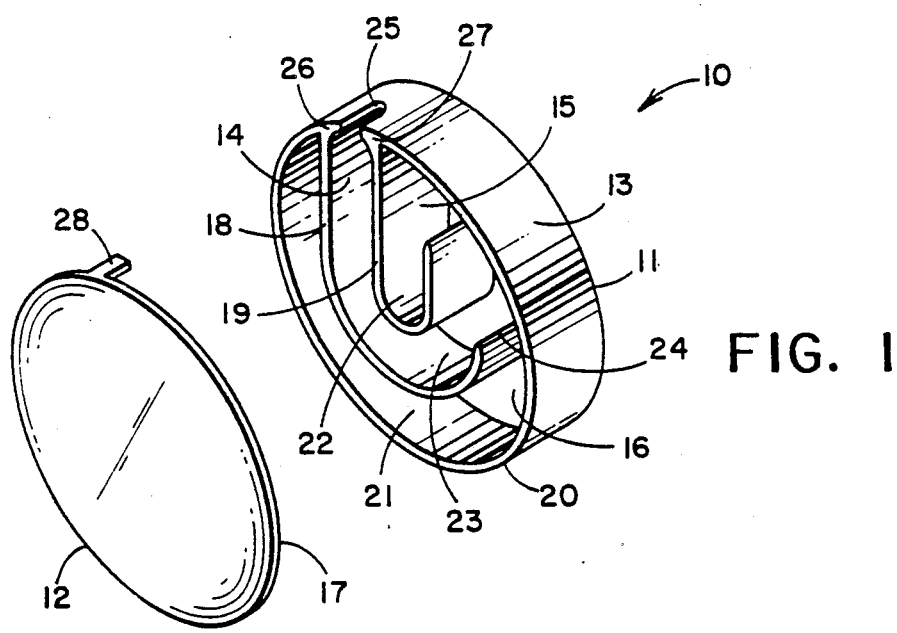
FIG. 1 is an exploded front perspective view of a preferred embodiment of the device of the present invention.
Figure 3:
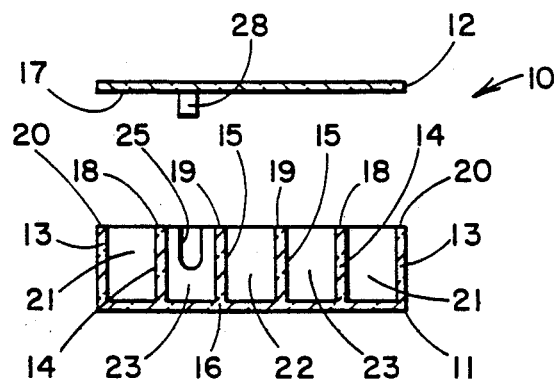
FIG. 3 is an exploded cross-sectional side view of the device taken along line 3—3 of FIG. 2 shown with a lid member.
Figure 3A:
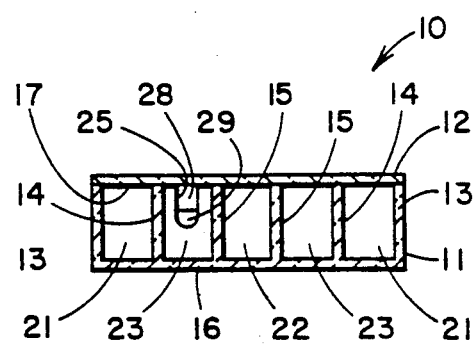
FIG. 3(a) is a cross-sectional side view of the device taken along line 3—3 of FIG. 2 shown with the lid member.

A particularly preferred form of the present device and its use in performing a sequential assay will now be described in order to provide a better understanding of the present invention. Referring to FIGS. 1-3, the device 10 of the present invention is preferably in the form of a closed, cylindrical vessel or container having a substantially horizontal axis of rotation and comprising an open body member 11 which is closed by a lid member 12 (FIGS. 3 and 3a). As will be described in greater detail hereinafter, body member 11 and lid member 12 are provided as separate components in order to permit the incorporation of one or more analytical reagents therein. Accordingly, once the analytical reagents have been incorporated into body member 11, body member 11 is closed by lid member 12 and permanently fastened thereto according to methods known in the art to provide a fluid-tight seal.

Body member 11 comprises a side wall 13 and first and second inner walls 14 and 15, respectively, situated on and positioned substantially perpendicular to an outer support wall 16. Side wall 13 and first and second inner walls 14 and 15 are substantially equal in height so that when body member 11 is closed by lid member 12, the inner surface 17 of the lid member 11 rests substantially against the upper edges 18 and 19 of first and second inner walls 14 and 15, respectively, and can be sealed against the upper edge 20 of side wall 13 in a fluid-tight manner.

Side wall 13 forms an analytical reagent reaction channel 21 which extends substantially around the periphery of body member 11 and opens into an analytical reaction viewing zone in the form of a viewing chamber 22 formed by second inner wall 15. Viewing chamber 22 serves as a cuvette for holding a liquid test sample or an analytical reaction mixture thereof during measurement of a detectable response and is situated at one end of, and in open liquid flow communication with, reaction channel 21. Preferably, viewing chamber 22 is disposed in a substantially central position in the device 10 wherein the horizontal axis of rotation of the device 10 intersects viewing chamber 22. Accordingly, the horizontal axis of rotation of the device 10 serves to align viewing chamber 22 with, for example, a light source or other energy path generated by an instrument known in the art, such as a spectrophotometer, for detecting and measuring the detectable response of an analytical reaction mixture in viewing chamber 22.

First inner wall 14 forms a delivery chamber 23 which provides for the unidirectional flow of a liquid test sample disposed therein into reaction channel 21. Delivery chamber 23 opens into reaction channel 21 and is situated substantially between viewing chamber 22 and reaction channel 21 in order that a liquid test sample disposed in delivery chamber 23 can be transported by gravity out of delivery chamber 23 and into reaction channel 21 by rotating the device 10 about the horizontal axis of rotation, as will be described in greater detail hereinafter.

It is to be understood that what is intended by open liquid flow communication is the ability of a liquid test sample or an analytical reaction mixture disposed in reaction channel 21 to be freely transported by gravity therealong, and to be freely and, if desired, repeatedly, transported by gravity between reaction channel 21 and viewing chamber 22, by rotating the device 10 about the horizontal axis of rotation. Conversely, what is intended by unidirectional flow of a liquid test sample from delivery chamber 23 is that although a liquid test sample disposed in delivery chamber 23 can be transported by gravity out of delivery chamber 23 and into reaction channel 21 by rotating the device 10 about the horizontal axis of rotation, the liquid test sample will not re-enter delivery chamber 23 upon subsequent rotations of the device 10 about the horizontal axis of rotation. As will be understood by one skilled in the art, the inability of a liquid test sample to re-enter delivery chamber 23 will, of course, depend upon the volume of the liquid test sample and the distance between the distal end 24 of first inner wall 14 and side wall 13.

Side wall 13 of body member 11 preferably includes an elongate opening 25 situated substantially between the proximal ends 26 and 27 of the first and second inner walls 14 and 15, respectively, which are connected to side wall 13. Opening 25 is configured to mateably receive a substantially flat, elongate pin 28 which extends from the edge of, and positioned substantially perpendicular to, lid member 12 wherein the length of pin 28 is shorter than the length of opening 25. Accordingly, when body member 11 is closed by lid member 12 with pin 28 inserted into opening 25, an inlet port 29 (FIG. 3a) is provided for introducing a liquid test sample into delivery chamber 23. It is to be understood that pin 28 is provided to conveniently align lid member 12 with body member 11 when body member 11 is closed with lid member 12 and then glued, laser welded, or otherwise sealed or fastened together, and is therefore not essential to the assembly of the device 10. However, where pin 28 is not provided, it is preferred that opening 25 be closed substantially at the area which would otherwise receive pin 28 in order to form inlet port 29 situated substantially as shown in FIG. 3a. It is preferable in either case that the location of inlet port 29 direct the introduction of a liquid test sample into delivery chamber 23, such as with a pipette inserted into inlet port 29, a distance away from the upper, inner surface of lid member 12 and the upper, inner surface of support wall 16 in delivery chamber 23. In this manner, a liquid test sample is prevented from substantially contacting the upper inner surfaces of lid member 12 and support wall 16 when introduced into the device 10 through inlet port 29. Accordingly, substantially all of the desired volume introduced into the device 10 drops freely by gravity into delivery chamber 23 without adhering to the upper inner surfaces of lid member 12 and support wall 16 as a result of, for example, surface tension.

As will be described in greater detail hereinafter, a liquid test sample disposed in delivery chamber 23 is transported by gravity out of delivery chamber 23 and into reaction channel 21 by rotating the device 10 in a clockwise direction about the horizontal axis of rotation. Once the liquid test sample has been transported into reaction channel 21, it can then be transported by gravity along reaction channel 21 in a direction away from or toward and, of course, into viewing chamber 22 in any desired sequence by simply rotating the device 10 in the appropriate direction. For example, a liquid test sample can be transported by gravity along reaction channel 21 in a direction away from viewing chamber 22 by rotating the device 10 in a counter-clockwise direction. Once the liquid test sample has been transported into reaction channel 21, it can then be transported by gravity along reaction channel 21 in a direction away from viewing chamber 22 by rotating the device 10 in a counter-clockwise direction, and in a direction toward viewing chamber 22 by rotating the device 10 in a clockwise direction.

It is to be understood that the operation of the device 10 as described above depends upon the substantially free gravitational flow of a liquid test sample or reaction mixture thereof disposed therein. As will be understood by one skilled in the art, such free gravitational flow can be substantially hindered by surface tension, air pockets, and other physical phenomena which frequently occur when a liquid is in substantial contact with one or more solid surfaces or for example when disposed in a capillary duct or the like. Accordingly, such free gravitational flow of a liquid test sample in the device 10 will depend upon the open, internal dimensions of reaction channel 21, viewing chamber 22 and delivery chamber 23, as well as the volume of the liquid test sample disposed therein. Such internal dimensions of the device will normally be of sufficient size to accomodate and, at the same time, vent the liquid test sample as it is manipulated throughout the device 10. Although the dimensions of the device 10 are preferably substantially of the size shown in the drawings, one skilled in the art apprised of the foregoing considerations can modify the dimensions of the device 10 or otherwise provide for the free gravitational flow of a liquid test sample therein. For example, the device 10 can include air vents or openings to permit the escape of air from the device 10 as the liquid test sample is manipulated therein and thereby prevent the formation of air pockets or prevent the occurrence of other physical phenomena which could otherwise hinder the free gravitational flow of the liquid test sample. Such vents or openings, of course, will be situated at an area or areas of device 10 or otherwise constructed to prevent the escape of a liquid test sample or reaction mixtures thereof from device 10.

In order to provide for the free gravitational flow of the liquid test sample or reaction mixtures thereof as described above, it is preferred that the volume thereof be less than that volume which will substantially occupy or fill the area of liquid flow movement between upper and lower walls thereof, such as, for example, the area between side wall 13 and first inner wall 14, and the area between first inner wall 14 and second inner wall 15. Preferably, a liquid test sample can be from between about 0.05 mL and about 1.0 mL, more preferably from between about 0.25 mL and about 0.75 mL, which can be freely transported in the device 10 in accordance with the teachings of the present invention. In addition, the surfaces within the device 10 can be treated according to methods known in the art to provide a wettable or hydrophilic surface in order to permit the free flow of a liquid test sample therealong and to substantially prevent surface tension or other physical phenomena from occurring. Such treatment of the surfaces includes, but is not intended to be limited to, plasma treatments such as plasma etching and plasma polymerization, corona discharge, wet chemical treatment and coating technologies known in the art, and the like.

It is to be understood that according to the present invention, the device is normally rotated about the horizontal axis for substantially short distances or increments so that the movement of a liquid sample disposed in the device is the result of the gravitational force exerted upon the liquid. Accordingly, the gravitational movement of a liquid in the device is accomplished by the non-centrifugal rotation of the device, and is not intended to be accomplished by centrifugal forces which would be greater than the gravitational force exerted upon the liquid. Preferably, the device as shown in rotated about the horizontal axis at from between about 1 r.p.m. and about 40 r.p.m. more preferably from between about 15 r.p.m. and about 30 r.p.m. Such non-centrifugal, rotational speed will of course depend upon the size of the device and can be determined by one skilled in the art apprised of the foregoing consideration.

Figure 4A:
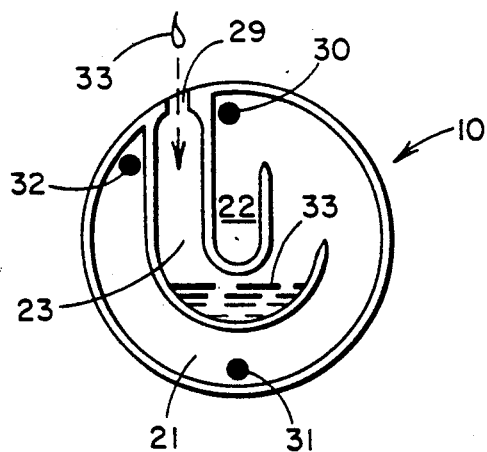

Referring now to FIGS. 4(a)–4(l), the device 10 is shown in various rotational positions to further illustrate the gravitational flow of a liquid medium and the sequential contact thereof with analytical reagents incorporated into reaction channel 21 when the device 10 is rotated about the horizontal axis of rotation as described above. The solid arrows shown outside the device 10 indicate the direction of rotation of the device 10 about the horizontal axis, and the broken arrows shown within the device 10 indicate the direction of liquid flow when the device 10 is rotated about the horizontal axis in the direction indicated by the solid arrows. It is to be understood that FIGS. 4(a)–4(l) are for purposes of illustration only, and are not intended to limit the number of analytical reagents which can be incorporated into the device 10 or the sequence and direction of rotation of the device 10. For example, although three reaction zones 30, 31 and 32 are shown in FIG. 4(a) to illustrate an assay protocol requiring three analytical reagents, less than or more than three reaction zones can be present, depending upon the number of analytical reagents necessary to carry out a particular assay. Furthermore, the device 10 can include less than the required number of analytical reagents for performing an analytical assay procedure wherein one or more reaction mixtures thereof can first be formed outside of the device 10 and then introduced into the device 10 to complete the assay. For example, where a particular assay requires three analytical reagents to perform the assay, the device 10 can be incorporated with two of the analytical reagents, wherein a reaction mixture comprising a liquid test sample and one of the analytical reagents is formed outside of the device 10 and then introduced therein to complete the assay with the two analytical reagents incorporated into the device 10.

As shown in FIG. 4(a), reaction channel 21 includes a first reaction zone 30 incorporated with a first analytical reagent, a second reaction zone 31 incorporated with a second analytical reagent, and a third reaction zone 32 incorporated with a third analytical reagent. As will be described in greater detail hereinafter, the analytical reagents are preferably present in reaction channel 21 in a substantially dry, water soluble, suspendable, or dissolvable form and can be incorporated therein according to methods known in the art, and are situated along reaction channel 21 in the desired order in which they are to be sequentially contacted with a liquid test sample.

A liquid test sample 33 containing an analyte is introduced into the device 10 through inlet port 29 and transported by gravity into delivery chamber 23 [FIG. 4(a)]. Liquid test sample 33 is transported by gravity out of delivery chamber 23 and into reaction channel 21 by rotating the device 10 in a clockwise direction [FIG. 4(b)], and then transported by gravity along reaction channel 21 and brought into contact with first reagent zone 30 by further rotating the device 10 in the same (clockwise) direction. The first analytical reagent is taken up by liquid test sample 33 to form a first reaction mixture 34 [FIG. 4(c)]. Preferably, the device 10 is oscillated in order to assure complete solubilization or suspension of the first analytical reagent [FIG. 4(d)] and, if desired, kept in a stationary position as shown in FIG. 4(c) for a predetermined incubation period to allow the analyte in the liquid test sample to sufficiently interact with the first analytical reagent. Where first reaction mixture 34 provides a first detectable response or measurable characteristic which is required or desired to be measured according to a particular assay protocol, the device 10 is still further rotated in the same (clockwise) direction in order that first reaction mixture 34 is transported by gravity into viewing chamber 22. Any such first detectable response provided by first reaction mixture 34 can then be detected and measured [FIG. 4(e)]. For example, such first detectable response can be a sample blank measurement or, a total hemoglobin measurement where the liquid test sample is a whole blood sample, such as when performing an assay for the percent of glycated hemoglobin in a whole blood sample, as will be described in greater detail hereinafter.

Figure 4B:
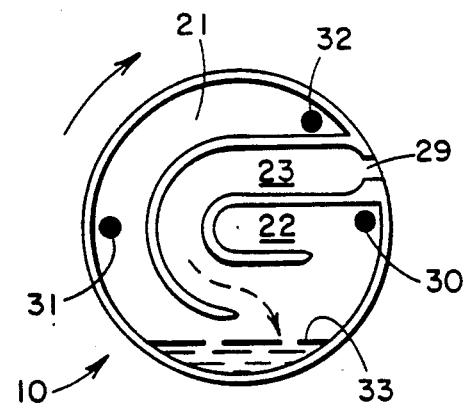
Figure 4C:
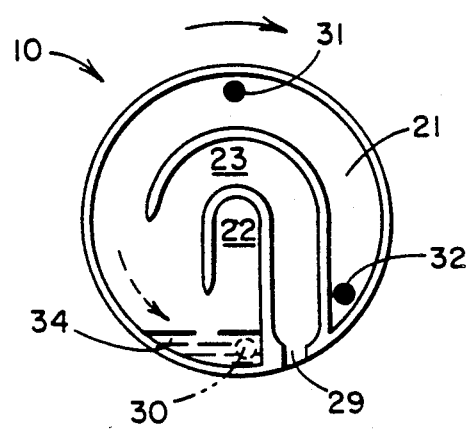
Figure 4D:
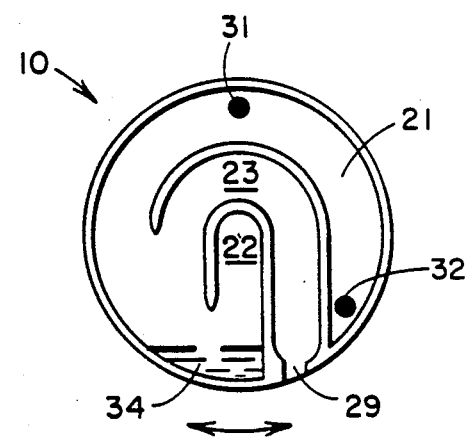
Figure 4E:
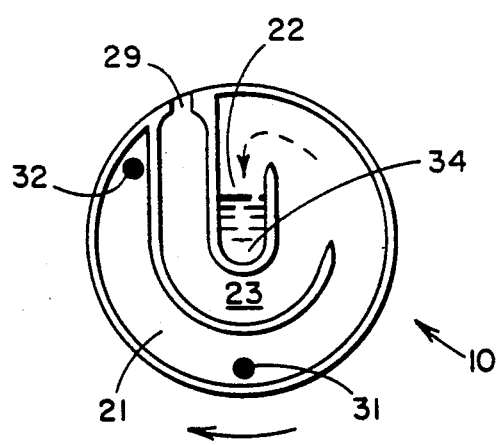
Figure 4F:
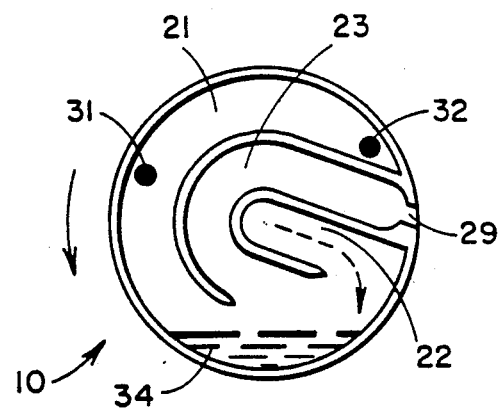

Once the first detectable response is detected and measured in viewing chamber 22, the device 10 is rotated in the same (clockwise) direction to transport reaction mixture 34 by gravity out of viewing chamber 22 and into reaction channel 21 [FIG. 4(f)]. First reaction mixture 34 is brought into contact with second reaction zone 31 by rotating the device 10 in the opposite (counter-clockwise) direction wherein first reaction mixture 34 is transported by gravity along reaction channel 21 to second reaction zone 31 to form a second reaction mixture 35 with the second analytical reagent incorporated therein [FIG. 4(g)] and, preferably incubated and oscillated [FIG. 4(h)] as described above. Referring again to FIG. 4(d), it is to be understood, of course, that where a first detectable response is not provided or is not necessary or desirable to measure as described above, first reaction mixture 34 can instead be directly transported along reaction channel 21 from first reaction zone 30 [FIG. 4(d)] to second reaction zone 31 [FIG. 4(g)] by rotating the device 10 in a counter-clockwise direction.

Similarly, second reaction mixture 35 is brought into contact with third reaction zone 32, if still present, by still further rotating the device 10 in the same (counter-clockwise) direction in order that second reaction mixture 35 is transported by gravity along reaction channel 21 to third reaction zone 32 to form a third reaction mixture 36 with the third analytical reagent incorporated therein [FIG. 4(i)] and, preferably incubated and oscillated [FIG. 4(j)] as described above. Typically, the final reaction mixture in an analytical assay procedure, in this case third reaction mixture 36, will provide a detectable response which is measured and correlated to the amount of analyte in the liquid test sample, or, where a first detectable response is provided as described above, measured and compared to the first detectable response as a function of the analyte. In either case, third reaction mixture 36 is returned to viewing chamber 22 by rotating the device 10 in a clockwise direction [FIGS. 4(k) and 4(l)].

The position of the reaction zones in reaction channel 21 are not intended to be limited to the positions as shown in FIG. 4(a), but can be situated on or at any surface along reaction channel 21 which will be contacted by the liquid test sample and analytical reaction mixtures thereof. For example, the reaction zones can be situated on one or all of the inner surface of side wall 13, lid member 12, or body member 11 at a desired location in reaction channel 21.

The analytical reagents can be incorporated into reaction channel 21 by non-covalent binding techniques, absorbtive techniques, and other methods known in the art. A reagent pad comprising, for example, an absorbtive material, such as a woven fabric, a bibulous material, and the like, or a reagent film, can be incorporated with an analytical reagent according to methods known in the art and attached to a surface of the reaction channel which is contacted with the liquid test sample. Although the analytical reagents are preferably incorporated in a dry form thereof, one or more liquid analytical reagents can be incorporated or prepackaged into one or more areas of the device and isolated or sealed with, for example, a membrane which is capable of being removed to release the liquid analytical reagent into the device prior to or during the performance of an assay.

It is to be understood that the device of the present invention is not intended to be limited as described above, and can be modified without departing from the teachings of the present invention. In addition to being in the form of a substantially cylindrical container as previously described, the device of the present invention can instead be square, rectangular, triangular, or the shape and configuration thereof otherwise modified without departing from the teachings of the present invention. Furthermore, the internal configuration of, for example, the walls of the device is not intended to be limited as previously described, and can either conform to the general shape and configuration of the device or can be substantially non-conforming. However, it is to be understood, of course, that such modifications will nevertheless at least provide a reaction channel along which a liquid test sample can be transported by gravity by rotating the device about the horizontal axis of rotation thereof, delivery means for providing unidirectional flow of a liquid test sample into the reaction channel, and inlet means for introducing a liquid test sample into the delivery means.

The delivery means can be in the form of a substantially longitudinal channel or other configuration which provides for the gravitational transport of a liquid test sample into the reaction channel without necessarily having to rotate the device, and will be situated relative to the reaction channel whereby a liquid test sample or reaction mixtures thereof disposed in the reaction channel will not re-enter the delivery means upon subsequent rotations of the device as described above. Although the inlet means is preferably in the form of a port provided in the side wall of the device as described above, the inlet means can be situated along the delivery means, such as in the support wall or the lid member, provided that, of course, a liquid test sample introduced therethrough and into the delivery means will not leak out of or otherwise exit the device through such inlet means, particularly during subsequent rotations of the device. Furthermore, although the viewing zone is preferably in the form of a viewing chamber as described above, it is to be understood that a viewing zone can be a predetermined area along and in the reaction channel from which a detectable response can be detected and measured. Alternatively, a viewing chamber can be in the form of, for example, an indentation or protrusion from the side wall of the device.

As will be understood by one skilled in the art, the movement of a liquid test sample throughout the device of the present invention is the result of the gravitational force on the liquid test sample as the device is rotated substantially about the horizontal axis as described above. Accordingly, such movement of a liquid test sample in the device does not require mechanically generated forces, such as centrifugal forces. Since the movement of a liquid test sample throughout the device according to the present invention is based upon the gravitational manipulation thereof, a liquid test sample disposed in the device will be supported by a lower surface, e.g., side wall 13, first inner wall 14, or second inner wall 15, between lid number 12 and support wall 16. It is to be understood that the movement of a liquid test sample throughout the device according to the present invention is substantially independent of an upper surface relative to the location of the liquid test sample in the device. For example, when disposed in reaction channel 21, the gravitational movement of the liquid test sample is independent from first inner wall 14 and, similarly, when disposed in delivery chamber 23, independent from second inner wall 15. Accordingly, first inner wall 14 is functional when supporting and guiding a liquid test sample therealong, and second inner wall 15 is functional when supporting and guiding a liquid test sample therealong, each of which walls are otherwise substantially non-functional.

Although reaction channel 21, delivery chamber 23, and viewing chamber 22 each functionally comprise three walls, i.e., side wall 13, first inner wall, and second inner wall 15, respectively, and outer wall 16 and lid member 12, the configuration of the functional walls along which a liquid test sample is guided and transported is not intended to be limited as shown and can be modified provided that they nevertheless serve to support and guide a liquid test sample therealong as described above. For example, one or more of side wall 13 and first and second inner walls 14 and 15 can be V-shaped, U-shaped, or otherwise configured to provide a trough-like channel or conduit for supporting and guiding a liquid test sample therealong.

Support wall 16 can instead be provided as a separate element as is lid member 12 wherein first and second inner walls 14 and 15 are integral with side wall 13 and closed by such separate support wall 16 and lid member 12. Such separate support wall 16 and lid member 12 can also be in the form of a thin, flexible membrane, film, or thin plastic which can be solvent welded, laser welded, glued, or otherwise attached to side wall 13. The device 10 can also be modified to include an additional open body member having substantially the same dimensions of body member 11 and adapted to be closed by support wall 16 of body member 11, similar to the manner by which body member 11 is closed by lid member 12, or, alternatively, closed by an additional lid member 12. Such additional body member can be adapted to include an extension of reaction channel 21 in order to accomodate additional analytical reagents by providing, for example, a port or opening in support wall 16 at the distal end 37 of the reaction channel 21. This will provide open liquid flow communication between reaction channel 21 and such extension thereof.

An absorptive metering pad or wick having a substantial liquid volume capacity can also be disposed in an extension of body member 11 and situated substantially adjacent to delivery chamber 23. Such metering means will be located to be in liquid flow contact with a liquid test sample disposed in delivery chamber 23 through a metering port or opening provided in support wall 16. The metering port can be situated at a predetermined level in support wall 16 such that the volume of a liquid test sample in delivery chamber 23 which is at or above such predetermined level will be absorbed by the metering means through the metering port. Accordingly, such metering means permits the introduction of only an approximate volume of a liquid test sample into delivery chamber 23 since any of the excess volume thereof will be absorbed by the metering pad to result in the desired final volume of the liquid test sample for performing an analytical assay procedure. As will be understood by one skilled in the art, the final volume of the liquid test sample in delivery chamber 23 would be determined, and controlled by, the volume capacity of delivery chamber 23 below the metering port.

Figure 5:
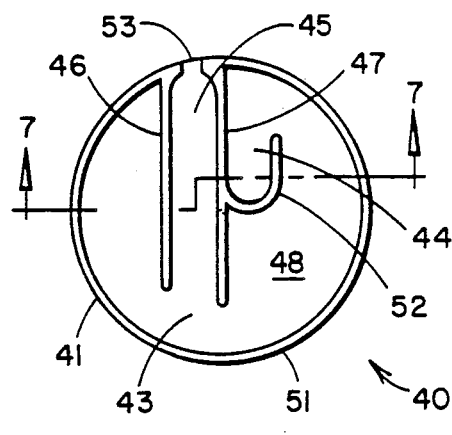
FIG. 5 is a front view of another embodiment of the device of the present invention without a lid member.

Additional embodiments which do not depart from the teachings of the present invention are shown in FIGS. 5 and 6 and FIGS. 9 and 10. In particular, there is shown in FIG. 5 an analytical reagent reaction vessel or device 40 comprising an open body member 41 which is closed by a lid member 42 (FIG. 7) as previously described. Body member 41 comprises a reaction channel 43 and a viewing chamber 44 in open liquid flow communication with reaction channel 43, and means for providing unidirectional flow of a liquid test sample into reaction channel 43 in the form of a delivery channel 45. Delivery channel 45 is defined by first and second inner walls 46 and 47 which are situated on and positioned substantially perpendicular to an outer wall 48. Reaction channel 43 is defined by a side wall 51 situated on and positioned substantially perpendicular to outer wall 48, with a curved wall 52 similarly situated and positioned on outer wall 48 to form viewing chamber 44. Body member 41 is closed by lid member 42 as described above, with side wall 51 of body member 41 including an elongate opening 53 and lid member 42 including an elongate pin 54 which is shorter than and inserted into opening 53 to provide an inlet port 55 (FIG. 7).

A liquid test sample introduced through inlet port 55 is directly transported by gravity into reaction channel 43 through delivery channel 45. The liquid test sample can then be transported by gravity along reaction channel 43 to sequentially contact the liquid test sample with one or more analytical reagents incorporated therein, and into viewing chamber 44, by rotating the device 40 about the horizontal axis of rotation thereof as previously described.

Figure 6:
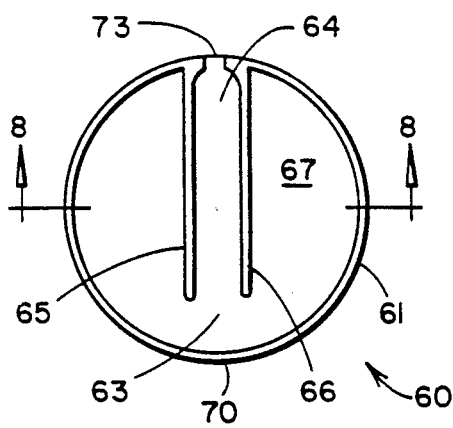
FIG. 6 is a front view of still another embodiment of the device of the present invention shown without a lid member.
Figure 8:
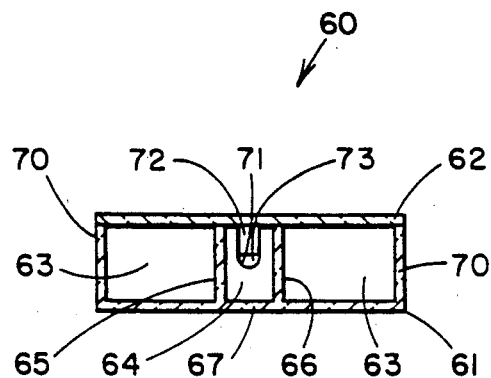
FIG. 8 is an exploded cross-sectional side view taken along line 8—8 of FIG. 6 shown with a lid member.
Figure 7:
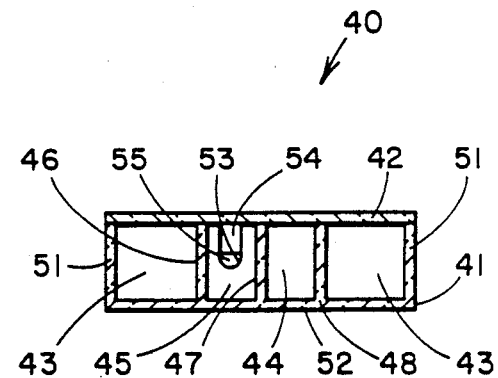
FIG. 7 is an exploded cross-sectional side view taken along line 7—7 of FIG. 5 shown with a lid member.

Similarly, there is shown in FIG. 6 an analytical reagent reaction vessel or device 60 comprising an open body member 61 which is closed by a lid member 62 (FIG. 8) as previously described, and which comprises a reaction channel 63 and a delivery channel 64. Delivery channel 64 is defined by first and second inner walls 65 and 66 which are situated on and positioned substantially perpendicular to an outer wall 67, and reaction channel 63 is defined by a side wall 70 similarly situated and positioned on outer wall 67. Body member 61 is closed by lid member 62 as described above, with side wall 70 of body member 61 including an elongate opening 71 and lid member 62 including an elongate pin 72 which is shorter than and inserted into opening 71 to provide an inlet port 73 (FIG. 8).

In this embodiment, the detectable response can be detected and measured from substantially any area or zone along reaction channel 63. Accordingly, once a liquid test sample has been introduced into reaction channel 63 through delivery channel 64 as described above, the device 60 is rotated about the horizontal axis of rotation wherein the liquid test sample can be transported by gravity along reaction channel 63 and sequentially contacted with one or more analytical reagents incorporated therein. A detectable response can be detected and measured from a desired, preferably predetermined, viewing zone location along reaction channel 63.

Figure 9:
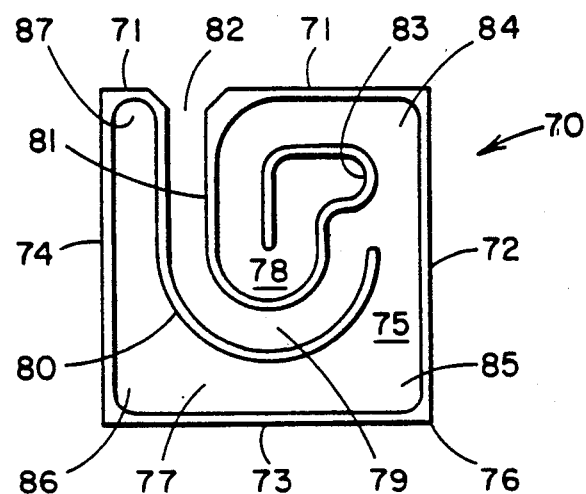
FIG. 9 is a front view of another embodiment of the device of the present invention without a lid member.

In addition, the device of the present invention can be substantially square wherein the corners formed by the side walls thereof serve to provide trough-like reaction or viewing areas. For example, there is shown in FIG. 9 a device 70 comprising four side walls 71, 72, 73 and 74, and an outer wall 75 which form a substantially square open body member 76 which is closed by a lid member (not shown) as previously described. Body member 76 comprises a reaction channel 77 formed by side walls 71, 72, 73 and 74, a viewing chamber 78 in open liquid flow communication with reaction channel 77, and a delivery chamber 79 for providing unidirectional flow of a liquid test sample into reaction channel 77. Delivery chamber 79 is formed by a first inner wall 80 and viewing chamber 78 is formed by a second inner wall 81, each of the walls 80 and 81 being situated on and positioned substantially perpendicular to outer wall 75. An inlet port 82 is provided in side wall 71 for introducing a liquid test sample into delivery chamber 79. The distal end of second inner wall 81 is configured as shown to provide a reagent zone in the form of a reagent chamber 83 which can be incorporated with an analytical reagent which can be contacted with a liquid test sample only upon substantial rotation of the device 70. Such reagent chamber 83 is particularly useful for incorporating an analytical reagent therein when it is desirable to prevent any contact thereof with a liquid test sample during the course of an assay, such as, for example, a detectant component which interacts with a detectable chemical group of a labeled reagent at the end of an assay.

Four corners 84, 85, 86 and 87 of the device 70 provide trough-like areas which can serve as reaction zones wherein analytical reagents can be incorporated into contactable surfaces of one or more of corners 84, 85, 86 and 87. Accordingly, a liquid test sample introduced into the device 70 can be transported along reaction channel 77 by gravity and contacted with analytical reagents incorporated in corners 84, 85, 86 and 87 by rotating the device 70 about the horizontal axis of rotation as described above.

Figure 10:
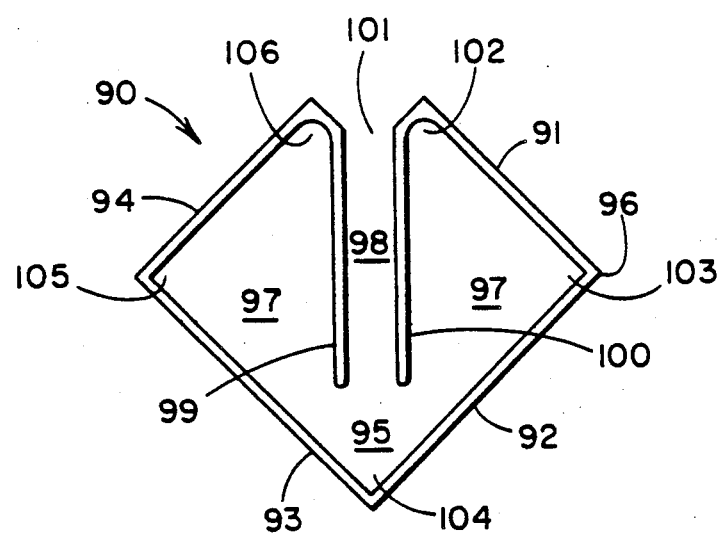
FIG. 10 is a front view of still another embodiment of the device of the present invention without a lid member.

In still another embodiment of the present invention, there is shown in FIG. 10 a device 90 comprising four side walls 91, 92, 93 and 94, and an outer wall 95 which form a substantially square open body member 96 which is closed by a lid member (not shown). Body member 96 comprises a reaction channel 97 formed by side walls 91, 92, 93 and 94, and a delivery channel 98 formed by first and second inner walls 99 and 100 for providing unidirectional flow of a liquid test sample into reaction channel 97. An inlet port 101 is provided between side walls 91 and 94 wherein a liquid test sample intoduced into delivery channel 98 through inlet port 101 is transported directly into reaction channel 97.

Five corners 102, 103, 104, 105 and 106 of the device 90 provide trough-like areas which can serve as reaction zones wherein analytical reagents can be incorporated into one or more contactable services thereof as described above. It is to be understood that any one of a predetermined corner 102, 103, 104, 105 or 106, preferably corner 104, can serve as a viewing zone or area. Accordingly, a liquid test sample introduced into the device 90 can be transported by gravity along reaction channel 97 and contacted with analytical reagents incorporated in one or more of corners 102, 103, 104, 105 or 106, and a detectable response generated therefrom detected and measured from a predetermined corner 102, 103, 104, 105 or 106.

Returning to the preferred embodiment depicted in FIGS. 1-4, the present device 10 is particularly useful for performing an immunoturbidimetric assay for determining hemoglobin A1c (HbA1c), a glycated hemoglobin derivative. According to such assay, hemoglobin in a whole blood sample is converted into a denatured thiocyan-met-hemoglobin form which serves as the basis for first measuring total sample hemoglobin, and then measuring the denatured HbA1c form by immunoassay. The immunoassay is based on the specific interaction of an antibody particle reagent and an agglutinator reagent, such as described by U.S. patent application Ser. Nos. 118,469; 118,476 and 118,566, filed Nov. 9, 1987.

The antibody particle reagent comprises an antibody, or a fragment thereof, specific for the glycated N-terminal peptide sequence in the beta-subunit of the denatured hemoglobin, bound to a water suspensible particle (e.g., a polystyrene or other latex). Such latex particles which are useful will be evident to the worker familiar with the field of latex agglutination immunoassays. In general, such particles require the properties necessary to serve as a stable support for the desired antibody reagent for the assay and to undergo agglutination in the presence of an agglutinator reagent sufficient for analytical purposes. Latex particles are prepared generally by emulsion polymerization or suspension polymerization [Bangs, L. G. (1984) Uniform Latex Particles, Seragen Diagnostics Inc., Indianapolis, IN U.S.A.]. Swollen emulsion polymerization can also be used [Ugelstad, J., et al (1980) Adv. Colloid and Interface Sci. 13:101-140]. A good selection of latex particles are commercially available. Polystyrene particles are particularly useful.

The attachment of the antibody reagent to the latex particles is a matter of applying conventional techniques. In general, the attachment can be covalent or noncovalent. The antibody reagent can consist of whole antibodies, antibody fragments, polyfunctional antibody aggregates, and the like. Normally, whole antibody or IgG fragments such as Fab, Fab', or F(ab')$_2$ are employed. The antibody reagent can be derived by any available technique such as conventional antiserum and monoclonal techniques.

The agglutinator reagent comprises a plurality of epitopic binding sites for the antibody reagent and can be prepared according to techniques familiar to the field of agglutination immunoassays. This reagent will, in general terms, comprise a plurality of epitopic binding sites for the anti-analyte antibody reagent. Such sites can be provided by using the analyte itself or a suitable analog that retains sufficient capacity to be bound by the antibody for purposes of an assay. Such analog can, in the case of a protein analyte, comprise a suitable fragment, prepared synthetically or by digestion, comprising the epitope for the antibody reagent, e.g., glycated peptide residues of hemoglobin A1c.

The aforementioned reagents can be incorporated into the device 10 in order that an immunoturbidimetric assay for HbA1c can be performed therein substantially as shown in FIGS. 4(a)-4(l). In particular, first reaction zone 30 can be incorporated with a dry, soluble form of a denaturant comprising a thiocyanate salt and an oxidant sufficient to convert the native hemoglobin ferrous ion to its ferric met-hemoglobin form; second reaction zone 31 can be incorporated with a dry, suspendable form of the antibody particle reagent; and third reaction zone 32 can be incorporated with a dry, soluble form of the agglutinator reagent. A whole blood test sample 33, or a pre-treated sample thereof, is introduced into delivery chamber 23 through inlet port 29 [FIG. 4(a)], and brought into contact with the denaturant in first reaction zone 30 to form a first reaction mixture 34 by rotating the device 10 in a clockwise direction [FIGS. 4(b)-4(d)], and preferably incubated for from between about 3-5 minutes, preferably at from between about 25° C. and about 39° C., more preferably at about 37° C. First reaction mixture 34 is then transported into viewing chamber 22 by further rotating the device 10 in a clockwise direction [FIG. 4(e)], and the total hemoglobin content determined by measuring the absorbance thereof, preferably at about 540 nm. First reaction mixture 34 is then brought into contact with the antibody particle reagent in second reaction zone 31 to form a second reaction mixture 35 by rotating the device 10 first in a clockwise direction [FIG. 4(f)], and then in a counter-clockwise direction [FIG. 4(g)]. Second reaction mixture 35 is preferably incubated as described above, and, if deisred, transported into viewing chamber 22 by rotating the device 10 in a clockwise direction (not shown) for a sample blank measurement. Second reaction mixture 35 is then brought into contact with the agglutinator in third reaction zone 32 to form a third reaction mixture 36 and incubated as described above by rotating the reaction vessel 10 in a counter-clockwise direction [FIGS. 4(i) and 4(j)]. The extent to which the antibody particle and agglutinator bind to one another to form a light scattering complex is dependent on the amount of HbAlc present and is readily quantitated by turbidimetric measurement.

The HbAlc measurement is then made by transporting third reaction mixture 36 into viewing chamber 22 by rotating the device 10 in a clockwise direction [FIGS. 4(k) and 4(l)]. The turbidity of third reaction mixture 36 is measured as described above. The turbidimetric response of third reaction mixture 36 and the total hemoglobin measurement of first reaction mixture 34 are correlated to the amount of HbAlc and total hemoglobin in the sample and the percent glycated hemoglobin in the whole blood test sample is then calculated.

The present device can be used to perform turbidimetric and nephelometric assays in general which are known in the art to determine analytes of interest in a variety of test samples, e.g., serum, plasma and urine. For example, agglutination immunoassays and agglutination inhibition immunoassays can be performed wherein the analytical reagents thereof are incorporated into the reaction channel in the desired order of sequence to be contacted by a liquid test sample.

According to another preferred embodiment of the present invention, the device is also useful for performing an immunometric assay involving binding among the analyte, a labeled reagent comprising an anti-analyte antibody reagent labeled with a detectable chemical group, and an immobilized form of the analyte or a binding analog thereof. According to such assay, the amount of labeled antibody reagent bound to the analyte from the liquid test sample or to that which is bound to the immobilized form of the analyte is determined and related to the amount of analyte present in the test sample.

The antibody component of the antibody reagent can be a whole antibody, such as any of the classes and subclasses of known immunoglobulins, e.g., IgG, IgM, and the like, or monovalent and divalent antibody fragments of IgG, conventionally known as Fab and Fab', and F(ab')$_2$, respectively. Preferably, the antibody will commonly be a divalent antibody fragment [F(ab')$_2$] or, more preferably, a monovalent antibody fragment (Fab or Fab'). Divalent and monovalent IgG antibody fragments can be obtained according to methods known in the art employing standard proteolytic digestion procedures with pepsin or papain.

The detectable chemical group of the labeled reagent can be any material having a detectable physical or chemical property. Such materials have been well-developed in the field of immunoassays and in general any label useful in such methods can be applied to such immunometric assay procedures. For example, such chemical groups having detectable physical properties are those groups which are detected on the basis of their own physical properties which do not require a chemical reaction or interaction with another chemical or substance to provide a detectable signal, such as fluorescers, phosphorescent molecules, chromophores, radioisotopes, spin labels, or electroactive moieties. Chemical groups having detectable chemical properties are those groups which are detected on the basis of their own chemical reactivity or interaction with a detectant component therefor to provide a detectable signal. Such chemical groups having detectable chemical properties do not generate a detectable product or otherwise provide a detectable signal prior to interacting with such detectant component, and include enzymatically active groups such as enzymes, enzyme substrates, coenzymes, enzyme inhibitors and activators, chemiluminescent species, chemical catalysts, metal catalysts, members of enzyme channeling, fluorophor-quencher, or energy transfer pairs, and specifically bindable ligands such as biotin or a hapten.

The immobilized form of the analyte or binding analog thereof can be immobilized or otherwise bound to a surface of reaction channel 21 in the area designated as second reaction zone 31 according to methods known in the art, or incorporated as an immobilized form into a reagent pad or film as described above.

Alternatively, the analyte or binding analog thereof can be immobilized to a magnetically responsive reagent particle which responds to a magnetic field without resultant permanent magnetization, commonly referred to as paramagnetic or paramagnetism. For example, such paramagnetic behavior is typically exhibited by iron oxides having a crystal size less than about 300 Å, whereas iron oxides having a crystal size greater than about 500 Å are characterized by responsiveness to a magnetic field with resultant permanent magnetization. Accordingly, such magnetically responsive reagent particles can be exposed to magnetic fields without becoming permanently magnetized, which would otherwise result in the undesirable magnetic aggregation thereof during the performance of an immunoassay.

Such magnetically responsive particles are known in the art and are commercially available, or can be prepared according to methods known in the art, such as described by U.S. Pat. No. 4,335,094 which employs a polymer having lattices or pores with a magnetic material deposited therein; U.S. Pat. Nos. 4,339,337 and 4,358,388 which employ a magnetic core surrounded by a vinylaromatic polymer; U.S. Pat. No. 4,452,773 which employs a colloidal magnetic iron oxide coated with a polysaccharide having pendant functional groups for covalently binding biological molecules thereto; and U.S. Pat. Nos. 4,554,088 and 4,628,037 which employ a metal oxide core generally surrounded by a silane coating.

Preferably, such uniform latex particles are dispersable or suspendable in aqueous media without significant gravitational settling and are therefore capable of remaining in suspension in the reaction mixture without constant mixing, i.e., water suspensible. Accordingly, together with Brownian motion and the high surface to volume ratio, efficient and rapid binding kinetics are assured.

The analyte or binding analog thereof can be immobilized to such paramagnetic particles according to methods known in the art. For example, where it is desirable to covalently bind the analyte or binding analog thereof to the magnetically responsive reagent particle, the particle should be polyfunctional or capable of being polyfunctionalized with functional groups which, for example, can be incorporated according to covalent coupling techniques known in the art [see for example, Cuatrecasas, *J. Biol. Chem.* Vol. 245, p. 3059 (1970)]. Functional groups include carboxylic acids, aldehydes, amines, amides, activated ethylenes such as maleimide, hydroxyls, sulfonic acids, mercaptans, and the like. For example, coupling of analytes and other biological molecules to agarose and polyacrylamides is described by W. B. Jacoby and M. Wilchek, *Methods in Enzymology*, Vol. 34, Academic Press, New York (1974).

Where an immunometric assay as described above is performed employing the device 10 of the present invention, first reaction zone 30 can be incorporated with a dry, soluble form of the anti-analyte antibody reagent, and second reaction zone 31 can be incorporated with an immobilized form of the analyte or binding analog thereof which is immobilized to an inner surface of or onto support wall 16, side wall 13 or lid member 12. Alternatively, where the analyte or binding analog is immobilized to a paramagnetic reagent particle as described above, such paramagnetic reagent particle is incorporated in a dry, suspendable form and, when suspended by a liquid test sample or reaction mixture thereof, is magnetically retained when it is desired to prevent the free movement thereof along reaction channel 21. Third reaction zone 32 can be incorporated with a dry, soluble form of a detectant component where the detectable chemical group of the labeled reagent possesses a detectable chemical property as described above. Accordingly, it is to be understood that where the detectable chemical group of the labeled reagent possesses a detectable physical property as described above, a third reaction zone 32 would not be required. Furthermore, where the detectable chemical group of the labeled reagent possesses a detectable chemical property and the analyte or binding analog thereof is immobilized to a paramagnetic reagent particle as described above, third reaction zone 32 is preferably situated at a lower portion of viewing chamber 22, or a reagent chamber can be provided, such as reagent chamber 83 depicted in FIG. 9, in order to prevent the interaction of the detectant component incorporated therein with the detectable chemical group of the labeled reagent which may be bound to the analyte immobilized to the paramagnetic reagent particle during the course of the assay.

In carrying out such immunometric assay with the analytical reagents incorporated into the device 10 as described above, a liquid test sample 33, such as urine, serum, plasma, or other biological fluid or dilution thereof, is introduced into delivery chamber 23 through inlet port 29 [FIG. 4(a)], and brought into contact with the labeled reagent in first reaction zone 30 to form a first reaction mixture 34 by rotating the device 10 in a clockwise direction [FIGS. 4(b) and 4(c)] and incubated as described above [FIG. 4(d)]. First reaction mixture 34 is then transported along reaction channel 21 and brought into contact with the immobilized form of the analyte or binding anlog thereof in second reaction zone 31 to form a second reaction mixture 35 [FIG. 4(g)] by rotating the device 10 [FIG. 4(d)] in a counter-clockwise direction [FIG. 4(g)] and incubated as described above [FIG. 4(h)]. Accordingly, any of the free species of the labeled reagent becomes bound to and immobilized by the analyte or binding analog immobilized in second reaction zone 10, the bound species of the labeled reagent remaining the liquid medium as a freely transportable species.

Where the detectable chemical group of the labeled reagent possesses a detectable physical property, second reaction mixture 35 [FIG. 4(g)] containing the bound species of the labeled reagent is instead transported by gravity along reaction channel 21 and into viewing chamber 22 by rotating the device 10 in a clockwise direction. The detectable physical property of second reaction mixture 35 produced by the bound species of the labeled reagent in viewing chamber 22 is then measured and correlated to the amount of analyte in the liquid test sample according to methods known in the art. It is to be understood that where the analyte or binding analog thereof is immobilized to a paramagnetic reagent particle in second reaction zone 31 and therefore present in a suspended and freely transportable form in second reaction mixture 35, the paramagnetic reagent particle is magnetically retained prior to rotating the device 10 when transporting second reaction mixture 35 to viewing chamber 22. In this manner, the bound species is separated from the free species of the labeled reagent immobilized to the paramagnetic reagent particle wherein the paramagnetic reagent particle is prevented from being transported into viewing chamber 22, and wherein the bound species can be freely and transported into viewing chamber 22 for measuring the detectable response produced therefrom.

On the other hand, where the detectable chemical group of the labeled reagent possesses a detectable physical property, second reaction mixture 35 is brought into contact with the detectant component in third reaction zone 32 by rotating the device 10 in a counter-clockwise direction [FIG. 4(i)] and incubated as described above [FIG. 4(j)] to form third reaction mixture 36 which produces the detectable response as a result of the interaction thereof with the detectable chemical group of the labeled reagent. Third reaction mixture 36 is similarly transported into viewing chamber 22 by rotating the device 10 in a clockwise direction [FIGS. 4(k) and 4(l)], and the detectable response measured therefrom. It is to be understood that where a paramagnetic reagent particle is employed, third reaction zone 32 incorporated with the detectant component is preferably situated in a lower portion of viewing chamber 22 to form the third reaction mixture 36 therein, and the paramagnetic reagent particle is magnetically retained prior to transporting second reaction mixture 35 into viewing chamber 22 as described above.

The immunoassay methods described above can be used in the determination of a variety of analytes. The analyte usually is a peptide, polypeptide, protein, carbohydrate, glycoprotein, steroid, nucleic acid or other organic molecule for which a binding counterpart exists or which is producible in biological systems or can be synthesized. The analyte, in functional terms, is usually selected from the group comprising antigens, haptens, complementary polynucleotide sequences, hormones, vitamins, metabolites and pharmacological agents. Usually, the analyte is an immunologically-active polypeptide or protein, usually having a molecular weight of between about 1,000 and about 10,000,000, such as an antigenic polypeptide or protein, or a hapten having a molecular weight of at least about 100, and usually less than about 1,500.

Representative polypeptide analytes are angiotensin I and II, C-peptide, oxytocin, vasopressin, neurophysin, gastrin, secretin, bradykinin, and glucagon.

Representative protein analytes include the classes of protamines, mucoproteins, glycoproteins, globulins, albumins, scleroproteins, phosphoproteins, histones, lipoproteins, chromoproteins, and nucleoproteins. Examples of specific proteins are prealbumin, α-lipoproteins, human serum albumin, α-acid glycoprotein, $\alpha_1$-antitrypsin, $\alpha_1$-glycoprotein, transcortin, thyroxine binding globulin, haptoglobin, hemoglobin, glycated peptide sequences such as the glycated N-terminal peptide sequence in the beta-subunit of human hemoglobin, myoglobulin, ceruloplasmin, $\alpha_2$-macroglobulin, β-lipoprotein, erythopoietin, transferrin, hemopexin, fibrinogen, the immunolobulins such as IgG, IgM, IgA, IgD, and IgE, and their fragments, e.g., Fc and Fab' complement factors, prolactin, blood clotting factors such as fibrinogen, thrombin and so forth, insulin, melanotropin, somatotropin, thyrotropin, follicle stimulating hormone, leutinizing hormone, gonadotropin, human chorionic gonadotropin, thyroid stimulating hormone, placental lactogen, instrinsic factor, transcobalamin, serum enzymes such as alkaline phosphatase, lactic dehydrogenase, amylase, lipase, phosphatases, cholinesterase, glutamic oxaloacetic transaminase, glutamic pyruvic transaminase, and uropepsin, endorphins, enkephalins, protamine, tissue antigens, bacterial antigens, viral antigens such as hepatitis associated antigens (e.g., $Hb_sAg$, $HB_cAg$ and $HB_eAg$), and tumor markers (e.g., CEA, alpha fetoprotein, prostatic acid phosphatase, prostatic specific antigen, neuron specific enolase, estrogen receptor, CA125, CA19-9, and the like).

Representative hapten analytes include the general classes of drugs, metabolites, hormones, vitamins, toxins and the like organic compounds. Haptenic hormones include thyroxine and triiodothyronine. Vitamins include vitamins A, B, e.g., thiamine, $B_{12}$, C, D, E and K, and folic acid. Drugs include antibiotics such as aminoglycosides e.g., gentamicin, tobramycin, amikacin, sisomicin, kanamycin, and netilmicin, penicillin, tetracycline, terramycine, chloromycetin, and actinomycetin; nucleosides and nucleotides such as adenosine diphosphate (ADP) adenosine triphosphate (ATP), flavin mononucleotide (FMN), nicotinamide adenine dinucleotide (NAD) and its phosphate derivative (NADP), thymidine, guanosine and adenosine; prostaglandins; steroids such as the estrogens, e.g., estriol and estradiol, sterogens, androgens, digoxin, digitoxigenin, digitoxin, digoxigenin, 12-0-acetyldigoxigenin, and adrenocortical steroids; and others such as phenobarbital, phenytoin, primidone, ethosuximide, carbamazepine, valproate, theophylline, caffeine, propranolol, procainamide, quinidine, amitryptiline, cortisol, desipramine, disopyramide, doxepin, doxorubicin, nortryptiline, methotrexate, imipramine, lidocaine, procainamide, N-acetylprocainamide, amphetamines, catecholamines, and antihistamines. Toxins include acetyl T-2 toxin, alfatoxin, cholera toxin, citrinin, cytochalasins, staphylococcal enterotoxin B, HT-2 toxin, and the like.

It is further to be understood that the device of the present invention is not intended to be limited to performing such assay procedures as specifically described above, but can also be incorporated with analytical reagents for performing a variety of other assay procedures known in the art. For example, such other assay procedures include, but are not intended to be limited to, apoenzyme reactivation immunoassay system (ARIS) as described by U.S. Pat. No. 4,238,565; substrate labeled fluorescent immunoassay (SLFIA) as described by U.S. Pat. No. 4,279,992; enzyme inhibitor-labeled immunoassay as described by U.S. Pat. No. 4,134,792; enzyme multiplied immunoassay technique (EMIT ®) as described by U.S. Pat. Nos. 3,817,837 and 4,043,872; and fluorescence polarization immunoassay (TDX ®) as described by U.S. Pat. No. 4,510,251; and the like.

The device can be manually manipulated as described above and the detectable response provided by one or more of the reaction mixtures detected and measured with an optical instrument known in the art, such as by transmission absorption or scatter, and the like. It is to be understood that the body member and the lid member are made to be transparent, at least in the area of the viewing chamber, to provide a viewing window to permit such optical measurement of the reaction mixtures. Where the device is manually manipulated, the support wall and the lid member are preferably transparent substantially in their entirety in order to permit an operator to observe the movement and positioning of a liquid test sample disposed in the reaction vessel.

Preferably, the device is manipulated with a simple mechanical, non-centrifugal, rotating device which is adapted to receive the device in a substantially vertically orientated position as shown throughout the drawings, and which non-centrifugally rotates the device as described above employing, for example, but not intended to be limited to, rollers which frictionally engage the side wall. The rollers are operated by, for example, an electric stepping motor which, in turn, is controlled by a microprocessor programmed to rotate the device in the desired direction and in the desired order of sequence, including stationary positions for periods of incubation, and detection and measurement of one or more of a detectable response. Such mechanical device would also include an optical system for detecting and measuring the detectable response, such as a transmission absorption or scatter optical system, which is situated in the mechanical device substantially at the horizontal axis of rotation of the device, i.e., aligned with the viewing chamber. Such mechanical device could also include heating elements, such as stationary heaters or the rotating contact plate type having flexpoint connections, for heating a liquid test sample or reaction mixtures when required by a particular assay protocol, and optical sensors for properly positioning the device in the mechanical device. Preferably, the various mechanical and electronic components are housed in a conveniently sized case including, for example, a slot or opening for receiving a device or, where it is desired to simultaneously perform an assay protocol on more than one liquid test samples, more than one device of the present invention.

The device of the present invention can be molded or otherwise made from various moldable materials known in the art which include, but are not intended to be limited to, plastics such as polystyrene, acrylic, polycarbonate, glass, and the like. It is to be understood that although wettable or hydrophilic materials are preferred, non-wettable or hydrophobic materials can be employed which have been pretreated as described above.

It will be apparent that other modifications and variations of the invention as herein set forth are possible without departing from the spirit and scope thereof, and that, accordingly, such limitations are imposed only as indicated by the appended claims.

What is claimed is:

1. A method for performing sequential analytical reactions to determine an analyte in a liquid test sample, said method comprising the steps of:

(a) providing a closed analytical reagent reaction vessel having a substantially horizontal axis of rotation and comprising (i) an analytical reagent reaction channel comprising first and second reaction zones incorporated with first and second analytical reagents which interact with an analyte in a liquid test sample to produce a detectable response as a function of the analyte, said second reaction zone being situated a predetermined distance away from and in open liquid flow communication with said first reaction zone whereby a liquid test sample disposed in said reaction channel is capable of being transported by gravity along said reaction channel between said reaction zones by rotating said reaction vessel about said horizontal axis; (ii) liquid test sample delivery means for providing unidirectional flow of said liquid test sample into said reaction channel; and (iii) inlet means in open liquid flow communication with said delivery means for introducing a liquid test sample into said delivery means;

(b) introducing a liquid test sample into said reaction vessel through said inlet means;

(c) bringing said liquid test sample into contact with said first analytical reagent in said first reaction zone to form a first reaction mixture;

(d) rotating said reaction vessel about said horizontal axis whereby said first reaction mixture is transported by gravity away from said first reaction zone along said reaction channel and into contact with said second analytical reagent in said second reaction zone to form a second reaction mixture; and (e) measuring said detectable response.

2. The method of claim 1 wherein step (c) is accomplished by rotating said reaction vessel about said horizontal axis whereby said liquid test sample is transported by gravity along said reaction channel and into contact with said first analytical reagent.

3. The method of claim 1 wherein said liquid test sample introduced into said reaction vessel in step (b) flows through said delivery means and into said reaction channel by gravity.

4. The method of claim 1 wherein said reaction channel further comprises an analytical reaction mixture viewing zone in open liquid flow communication with said first and second reaction zones.

5. The method of claim 4 wherein said viewing zone is situated at one end of said reaction channel.

6. The method of claim 4 comprising the step of rotating said reaction vessel about said horizontal axis whereby said second reaction mixture is transported by gravity away from said second reaction zone along said reaction channel into said analytical reaction mixture viewing zone.

7. The method of claim 4 wherein said analytical reaction mixture viewing zone is in the form of a viewing chamber.

8. The method of claim 1 wherein said delivery means is in the form of a delivery chamber whereby said liquid test sample is transported by gravity out of said delivery chamber into said reaction channel by rotating said reaction vessel about said horizontal axis.

9. The method of claim 1 wherein said reaction zones are incorporated with a dried form of said analytical reagents.

10. A method for performing sequential analytical reactions to determine an analyte in a liquid test sample, said method comprising the steps of:

(a) providing a closed analytical reagent reaction vessel having a substantially horizontal axis of rotation and incorporated with analytical reagents which interact with an analyte in a liquid test sample to produce a detectable response as a function of the analyte, said reaction vessel comprising (i) an analytical reagent reaction channel situated in a plane of rotation about said horizontal axis and comprising (1) first and second reaction zones incorporated with first and second analytical reagents, said second reaction zone being situated a predetermined distance away from and in open liquid flow communication with said first reaction zone whereby a liquid test sample disposed in said reaction channel is transported by gravity along said reaction channel between said reaction zones by rotating said reaction vessel about said horizontal axis, and (2) an analytical reaction mixture viewing chamber in open liquid flow communication with said reaction zones; (ii) a liquid test sample delivery chamber for providing unidirectional flow of said liquid test sample into said reaction channel; and (iii) an inlet port for introducing a liquid test sample into said delivery chamber;

(b) introducing a predetermined amount of a liquid test sample into said delivery chamber through said inlet port;

(c) rotating said reaction vessel about said horizontal axis whereby said liquid test sample is transported by gravity out of said delivery chamber into said reaction channel and to said first reaction zone, thereby into contact with said first analytical reagent to form a first reaction mixture;

(d) rotating said reaction vessel about said horizontal axis whereby said second reaction mixture is transported by gravity away from said first reaction zone along said reaction channel to said second reaction zone, thereby into contact with said second analytical reagent to form a second reaction mixture;

(e) rotating said reaction vessel about said horizontal axis whereby said second reaction mixture is transported by gravity away from said second reaction zone along said reaction channel and into said viewing chamber; and (f) measuring said detectable response.

11. The method of claim 10 wherein said reaction zones are incorporated with a dried form of said analytical reagents.

12. The method of claim 10 wherein said viewing chamber is situated at one end of said reaction channel.

13. The method of claim 12 wherein said first reaction zone is situated substantially adjacent to said viewing chamber.

14. The method of claim 10 wherein said viewing chamber is disposed in a central position in said reaction vessel, said horizontal axis intersecting said viewing chamber.

15. The method of claim 10 wherein said first analytical reagent comprises a dry, disolvable antibody reagent comprising an antibody to said analyte, or a fragment thereof, labeled with a detectable chemical group and said second analytical reagent comprises an immobilized form of said analyte or a binding analog thereof.

16. The method of claim 15 wherein said analyte or binding analog thereof is immobilized to a surface of said second reaction zone.

17. The method of claim 15 wherein said analyte or binding analog thereof is immobilized to a suspendable particle.

18. The method of claim 15 wherein said analyte or binding analog thereof is immobilized to a suspendable, magnetizable particle.

19. The method of claim 15 wherein said detectable chemical group provides a physical property which produces said detectable response.

20. The method of claim 10 wherein said reaction channel comprises a third reaction zone incorporated with a third analytical reagent, said third reaction zone being situated a predetermined distance away from and in open liquid flow communication with said second reaction zone.

21. The method of claim 20 comprising the additional steps of rotating said reaction vessel about said horizontal axis whereby said second reaction mixture is transported away from said second reaction zone along said reaction channel to said third reaction zone and into contact with said third analytical reagent to form a third reaction mixture, and rotating said reaction vessel about said horizontal axis whereby said third reaction mixture is transported by gravity away from said third reaction zone along said reaction channel into said viewing chamber.

22. The method of claim 20 wherein said first analytical reagent comprises a dry, disolvable antibody reagent comprising an antibody to said analyte, or a fragment thereof, labeled with a detectable chemical group which interacts with a detectant component to produce a product which provides said detectable response, said second analytical reagent comprises an immobilized form of said analyte or a binding analog thereof, and said third analytical reagent comprises a dry, disolvable form of said detectant component.

23. The method of claim 20 wherein said analyte is glycated hemoglobin, said liquid test sample is a whole blood sample, and said first analytical reagent comprises a dry, disolvable denaturant reagent for determining the total hemoglobin concentration of said whole blood test sample, said second analytical reagent comprises an immobilized antibody reagent comprising an antibody to said analyte, or a fragment thereof, immobilized to a suspendable particle, and said third analytical reagent comprises a dry, disolvable agglutinating reagent which specifically binds to said antibody to produce a turbidimetric response as a function of the amount of glycated hemoglobin in said whole blood sample.

24. The method of claim 23 wherein the relative amount of glycated hemoglobin in said whole blood sample is determined by independently measuring the total hemoglobin concentration and the amount of glycated hemoglobin in the sample and calculating the percent of glycated hemoglobin.

25. The method of claim 23 wherein said particle is a water suspendable latex particle.

26. A method for performing sequential analytical reactions to determine an analyte in a liquid test sample, said method comprising the steps of:
(a) providing a closed analytical reagent reaction vessel having a substantially horizontal axis of rotation and comprising (i) an analytical reagent reaction channel comprising a reaction zone incorporated with an analytical reagent which interacts with an analyte in a liquid test sample to produce a detectable response as a function of the analyte, (ii) liquid test sample delivery means for providing unidirectional flow of said liquid test sample into said reaction channel; and (iii) inlet means in open liquid flow communication with said delivery means for introducing a liquid test sample into said delivery means;
(b) introducing a liquid test sample into said reaction vessel through said inlet means;
(c) measuring a determinable characteristic of said liquid test sample;
(d) rotating said reaction vessel about said horizontal axis whereby said liquid test sample is transported by gravity along said reaction channel and into contact with said analytical reagent in said first reaction zone to form a reaction mixture;
(e) measuring said detectable response provided by said reaction mixture; and
(f) correlating said determinable characteristic of said liquid test sample and said detectable response to the amount of said analyte present in said liquid test sample.

27. The method of claim 26 wherein said reaction vessel further comprises a viewing zone, said viewing zone being situated a predetermined distance away from and in open liquid flow communication with said reaction zone whereby a liquid test sample disposed in said reaction channel is capable of being transported by gravity along said reaction channel between said reaction zone and said viewing zone by rotating said reaction vessel about said horizontal axis.

28. The method of claim 27 comprising the step of rotating said reaction vessel about said horizontal axis whereby said liquid test sample is transported by gravity along said reaction channel to said viewing zone and said determinable characteristic measured from said viewing zone.

29. The method of claim 27 comprising the step of rotating said reaction vessel about said horizontal axis whereby said reaction mixture is transported by gravity along said reaction channel to said viewing zone and said detectable response measured therefrom.

30. The method of claim 26 wherein said viewing zone is situated at one end of said reaction channel.

31. The method of claim 26 wherein said viewing zone is in the form of a viewing chamber.

32. The method of claim 31 wherein said viewing chamber is disposed in a central position in said reaction vessel, said horizontal axis intersecting said viewing chamber.

33. The method of claim 26 wherein said delivery means is in the form of a delivery chamber whereby said liquid test sample is transported by gravity out of said delivery chamber into said reaction channel by rotating said reaction vessel about said horizontal axis.

34. The method of claim 26 wherein said first reaction zone is incorporated with a dried form of said analytical reagent.

35. The method of claim 26 wherein said measurement of said determinable characteristic is a sample blank measurement.

36. The method of claim 26 wherein said reaction channel is situated at and extends substantially around the periphery of said reaction vessel.

37. The method of claim 36 wherein said reaction vessel is in the form of a disk.

38. An analytical reagent reaction vessel for performing sequential analytical reactions to determine an analyte in a liquid test sample, said reaction vessel comprising a closed container having a substantially horizontal axis of rotation and comprising (a) an analytical reagent reaction channel comprising (i) first and second reaction zones incorporated with first and second analytical reagents which interact with an analyte in said liquid test sample to produce a detectable response as a function of the analyte, said second reaction zone being situated a predetermined distance away from and in open liquid flow communication with said first reaction zone, whereby a liquid test sample disposed in said reaction channel is transported by gravity along said reaction channel between said reaction zones and said viewing chamber by rotating said closed container about said horizontal axis, and (ii) an analytical reaction viewing zone in the form of a chamber in open liquid flow communication with said first and second reaction zones, (b) liquid test sample delivery means for providing unidirectional flow of a liquid test sample into said reaction channel; and (c) an inlet port for introducing a liquid test sample into said delivery means.

39. The reaction vessel of claim 38 wherein said reaction zones are incorporated with a dried form of said analytical reagent.

40. The reaction vessel of claim 38 wherein said delivery means is in the form of a delivery chamber whereby said liquid test sample is transported by gravity out of said delivery chamber into said reaction channel by rotating said reaction vessel about said horizontal axis.

41. The reaction vessel of claim 38 wherein said viewing chamber is situated at one end of said reaction channel.

42. The reaction vessel of claim 41 wherein said viewing chamber is situated substantially adjacent to said first reaction zone.

43. The reaction vessel of claim 41 wherein said viewing chamber is disposed in a central position in said vessel, said horizontal axis intersecting said viewing chamber.

44. The reaction vessel of claim 38 wherein said reaction channel is situated at and extends substantially around the periphery of said closed container.

45. The reaction vessel of claim 44 which is in the form of a disk.

46. The reaction vessel of claim 38 wherein said reaction channel comprises one or more additional reaction zones incorporated with one or more analytical reagents.

47. The reaction vessel of claim 38 wherein said first analytical reagent comprises a dry, disolvable antibody reagent comprising an antibody to said analyte, or a fragment thereof, labeled with a detectable chemical group and said second analytical reagent comprises an immobilized form of said analyte or a binding analog thereof.

48. The reaction vessel of claim 47 wherein said analyte or binding analog thereof is immobilized to a surface of said second reaction zone.

49. The reaction vessel of claim 47 wherein said analyte or binding analog thereof is immobilized to a suspendable particle.

50. The reaction vessel of claim 47 wherein said analyte or binding analog thereof is immobilized to a suspendable, magnetizable particle.

51. The reaction vessel of claim 46 wherein said reaction channel comprises a third reaction zone incorporated with a third analytical reagent, said third reaction zone being situated a predetermined distance away from and in open liquid flow communication with said second reaction zone.

52. The reaction vessel of claim 51 wherein said first analytical reagent comprises a dry, disolvable antibody reagent comprising an antibody to said analyte, or a fragment thereof, labeled with a detectable chemical group which interacts with a detectant component to produce a product which provides said detectable response, said second analytical reagent comprises an immobilized form of said analyte or a binding analog thereof, and said third analytical reagent comprises a dry, disolvable form of said detectant component.

53. The reaction vessel of claim 51 wherein said analyte is glycated hemoglobin, said liquid test sample is a whole blood sample, and said first analytical reagent comprises a dry disolvable denaturant reagent for determining the total hemoglobin concentration of said whole blood test sample, said second analytical reagent comprises a dry, disolvable antibody reagent comprising an antibody to said analyte, or a fragment thereof, immobilized to a suspendable particle, and said third analytical reagent comprises a dry disolvable agglutinating reagent which specifically binds to said antibody to produce a turbidimetric response as a function of the amount of glycated hemoglobin in said whole blood sample.

54. The reaction vessel of claim 53 wherein said suspendable particle is a water suspendable latex particle.

* * * * *